US011617820B2

(12) United States Patent
Fiering et al.

(10) Patent No.: US 11,617,820 B2
(45) Date of Patent: *Apr. 4, 2023

(54) SYSTEM FOR BLOOD SEPARATION BY MICROFLUIDIC ACOUSTIC FOCUSING IN SEPARATION CHANNELS WITH DIMENSIONS DEFINED BASED ON PROPERTIES OF STANDING WAVES

(71) Applicant: The Charles Stark Draper Laboratory, Inc., Cambridge, MA (US)

(72) Inventors: Jason O. Fiering, Boston, MA (US); Shivshanker Sundaram, Tampa, FL (US); Andrew Meuller, Somerville, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 895 days.

This patent is subject to a terminal disclaimer.

(21) Appl. No.: 16/236,404

(22) Filed: Dec. 29, 2018

(65) Prior Publication Data
US 2019/0388606 A1 Dec. 26, 2019

Related U.S. Application Data

(63) Continuation of application No. 14/772,216, filed as application No. PCT/US2014/022701 on Mar. 10, 2014, now Pat. No. 10,166,323.
(Continued)

(51) Int. Cl.
*B01D 21/28* (2006.01)
*A61M 1/36* (2006.01)

(52) U.S. Cl.
CPC .......... *A61M 1/3693* (2013.01); *A61M 1/362* (2014.02); *A61M 1/3678* (2014.02);
(Continued)

(58) Field of Classification Search
USPC ........ 210/85, 96.2, 251, 263, 513, 646, 647, 210/660, 666, 730, 748.02, 748.2;
(Continued)

(56) References Cited

U.S. PATENT DOCUMENTS 6,929,750 B2 8/2005 Laurell et al.
7,727,723 B2 6/2010 Pollack et al.
(Continued)

FOREIGN PATENT DOCUMENTS

EP 0 914 184 A1 5/1999
EP 1 809 399 B1 8/2009
(Continued)

OTHER PUBLICATIONS

Lenshof (Thesis, Acoustic Standing Wave Manipulation of Particles and Cells in Microfluidic Chips (2009)) (Year: 2009).*
(Continued)

*Primary Examiner* — Hayden Brewster
(74) *Attorney, Agent, or Firm* — Foley & Lardner LLP

(57) ABSTRACT

Systems and methods for cleansing blood are disclosed herein. The methods include acoustically separating undesirable particles bound to capture particles from formed elements of whole blood. After introducing the capture particles to whole blood containing undesirable particles, the whole blood and capture particles are flowed through a microfluidic separation channel. At least one bulk acoustic transducer is attached to the microfluidic separation channel. A standing acoustic wave, imparted on the channel and its contents by the bulk acoustic transducer, drives the formed elements and undesirable particles bound to capture particles to specific aggregation axes. After aggregating the particles, the formed elements exit the separation channel through a first outlet and are returned to the patient. The undesirable
(Continued)

particles, bound to the capture particles, exit through a second outlet and can be discarded to saved for later study.

13 Claims, 8 Drawing Sheets

Related U.S. Application Data

(60) Provisional application No. 61/775,233, filed on Mar. 8, 2013.

(52) U.S. Cl.
CPC ............ *A61M 1/3692* (2014.02); *B01D 21/28* (2013.01); *B01D 21/283* (2013.01); *B01D 2221/10* (2013.01)

(58) Field of Classification Search
USPC ........ 324/76.19, 113, 313, 318–322, 754.31; 340/854.6; 422/44
See application file for complete search history.

(56) References Cited

U.S. PATENT DOCUMENTS

| | | | |
|---|---|---|---|
| 7,815,871 B2 | 10/2010 | Pamula et al. | |
| 7,816,121 B2 | 10/2010 | Pollack et al. | |
| 7,901,947 B2 | 3/2011 | Pollack et al. | |
| 8,083,068 B2 | 12/2011 | Kaduchak et al. | |
| 9,731,062 B2 * | 8/2017 | Fiering | B01D 21/283 |
| 10,099,002 B2 | 10/2018 | Sun et al. | |
| 10,166,323 B2 | 1/2019 | Fiering et al. | |
| 2002/0009015 A1 | 1/2002 | Laugharn et al. | |
| 2002/0058273 A1 | 5/2002 | Shipwash | |
| 2003/0150792 A1 | 8/2003 | Koehler et al. | |
| 2003/0175947 A1 | 9/2003 | Liu et al. | |
| 2004/0005582 A1 | 1/2004 | Shipwash | |
| 2004/0069717 A1 | 4/2004 | Laurell et al. | |
| 2004/0091398 A1 | 5/2004 | Gilbert et al. | |
| 2004/0109793 A1 | 6/2004 | McNeely et al. | |
| 2005/0106064 A1 | 5/2005 | Laurell et al. | |
| 2008/0154535 A1 | 6/2008 | Sparks et al. | |
| 2008/0181828 A1 | 7/2008 | Kluck | |
| 2008/0217259 A1 | 9/2008 | Siversson | |
| 2010/0006501 A1 | 1/2010 | Laurell et al. | |
| 2010/0078384 A1 | 4/2010 | Yang | |
| 2010/0186524 A1 | 7/2010 | Ariessohn et al. | |
| 2010/0210989 A1 | 8/2010 | MacPherson et al. | |
| 2010/0317093 A1 | 12/2010 | Turewicz et al. | |
| 2011/0003303 A1 | 1/2011 | Pagano et al. | |
| 2011/0014297 A1 | 1/2011 | Lee et al. | |
| 2011/0034908 A1 | 2/2011 | Hyde et al. | |
| 2011/0045095 A1 | 2/2011 | Hettiarachchi et al. | |
| 2011/0136262 A1 | 6/2011 | Ragavan et al. | |
| 2011/0250585 A1 | 10/2011 | Ingber et al. | |
| 2012/0122084 A1 | 5/2012 | Wagner et al. | |
| 2012/0225475 A1 | 9/2012 | Wagner et al. | |
| 2013/0043170 A1 | 2/2013 | Rose et al. | |
| 2013/0048565 A1 | 2/2013 | Fiering et al. | |
| 2013/0085680 A1 | 4/2013 | Arlen et al. | |
| 2013/0156644 A1 | 6/2013 | Lee et al. | |
| 2014/0140891 A1 | 5/2014 | Fiering | |
| 2014/0209542 A1 | 7/2014 | Spain et al. | |
| 2014/0248621 A1 | 9/2014 | Collins | |
| 2015/0137015 A1 | 5/2015 | Toh et al. | |
| 2016/0008532 A1 | 1/2016 | Fiering et al. | |
| 2016/0030660 A1 | 2/2016 | Sun et al. | |

FOREIGN PATENT DOCUMENTS

| | | |
|---|---|---|
| EP | 2 145 687 A1 | 1/2010 |
| EP | 2 352 570 A2 | 8/2011 |
| WO | WO-98/46986 | 10/1998 |
| WO | WO-02/12896 | 2/2002 |
| WO | WO-02/29400 | 4/2002 |
| WO | WO-2006/032703 | 3/2006 |
| WO | WO-2006/114596 | 11/2006 |

OTHER PUBLICATIONS

Foreign Action other than Search Report on PCT PCT/US2018/029328 dated Nov. 7, 2019.
International Preliminary Report on Patentability dated Mar. 13, 2014 in PCT Application No. PCT/US2012/052886 (10 pages).
International Preliminary Report on Patentability dated Sep. 17, 2015 in PCT App No. PCT/US2014/022701.
International Search Report and Written Opinion for PCT/US2018/029328 dated Jun. 20, 2018.
International Search Report and Written Opinion in PCT/US2014/022701 dated Jul. 18, 2014.
International Search Report and Written Opinion dated Dec. 11, 2012 in PCT Application No. PCT/US2012/052886.
Non-Final Office Action on U.S. Appl. No. 15/962,420 dated Oct. 3, 2019.
Non-Final Office Action on U.S. Appl. No. 16/350,217 dated Oct. 3, 2019.
Notice of Allowance on U.S. Appl. No. 14/772,216 dated Aug. 27, 2018.
Notice of Allowance on U.S. Appl. No. 14/815,501 dated Jun. 13, 2018.
Notice of Allowance on U.S. Appl. No. 15/362,068 dated Jan. 26, 2018.
Notice of Allowance on U.S. Appl. No. 16/350,217 dated Jan. 13, 2020.
Office Action on U.S. Appl. No. 14/815,501 dated Feb. 8, 2018.
Requirement for Restriction/Election on U.S. Appl. No. 14/772,216 dated Jul. 21, 2017.
Requirement for Restriction/Election on U.S. Appl. No. 14/815,501 dated Oct. 4, 2017.
U.S. Non Final Office Action on U.S. Appl. No. 13/598,401 dated Jan. 2, 2015.
U.S. Notice of Allowance on U.S. Appl. No. 13/598,401 dated Jun. 2, 2017.
U.S. Notice or Allowance on U.S. Appl. No. 14/168,822 dated Aug. 3, 2016.
U.S. Notice of Allowance on U.S. Appl. No. 14/168,822 dated Mar. 7, 2016.
U.S. Office Action in U.S. Appl. No. 13/598,401 dated Jul. 1, 2015.
U.S. Office Action on U.S. Appl. No. 13/598,401 dated Jan. 30, 2017.
U.S. Office Action on U.S. Appl. No. 13/598,401 dated May 20, 2016.
U.S. Office Action on U.S. Appl. No. 14/772,216 dated Dec. 26, 2017.
U.S. Office Action on U.S. Appl. No. 15/362,068 dated Jul. 11, 2017.

* cited by examiner

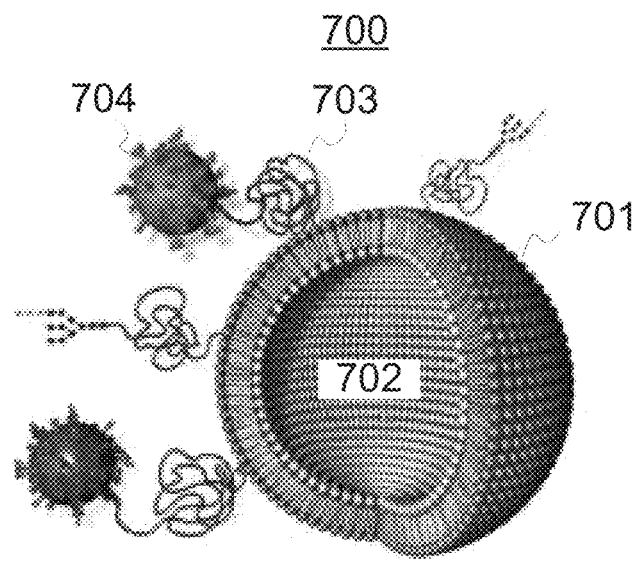
FIG. 7
FIG. 8A
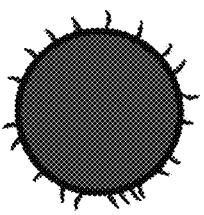
FIG. 8B
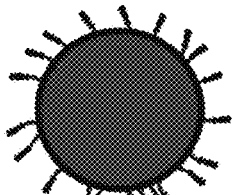
FIG. 8C
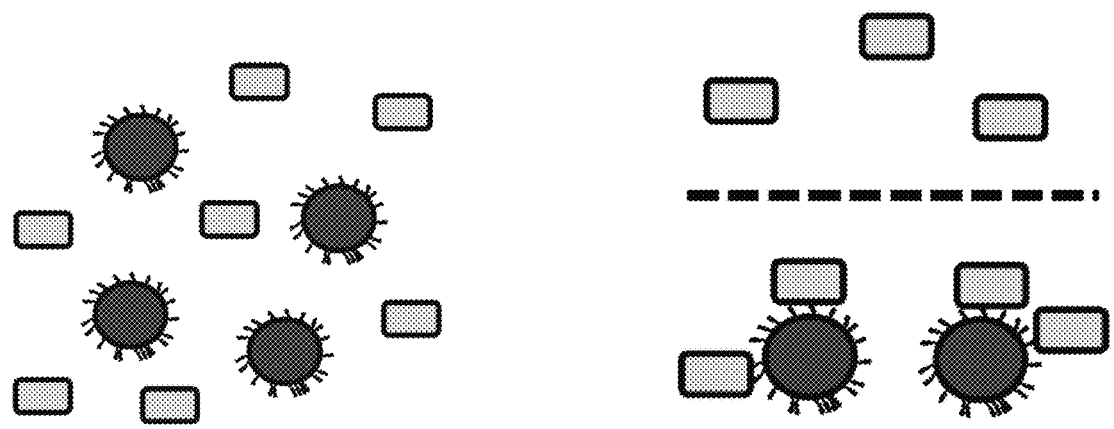
FIG. 8D
FIG. 8E

SYSTEM FOR BLOOD SEPARATION BY MICROFLUIDIC ACOUSTIC FOCUSING IN SEPARATION CHANNELS WITH DIMENSIONS DEFINED BASED ON PROPERTIES OF STANDING WAVES

RELATED CASES

The present application is a continuation of, and claims priority to, U.S. patent application Ser. No. 14/772,216, filed Sep. 2, 2015, which is a U.S. National Stage Application of, and claims priority to, International Application No. PCT/US2014/022701, filed on Mar. 10, 2014, which claims priority to U.S. Provisional Patent Application No. 61/775,233, filed on Mar. 8, 2013, and titled "System and Method For Blood Separation by Microfluidic Acoustic Focusing," which is incorporated herein by reference in its entirety.

BACKGROUND OF THE DISCLOSURE

Sepsis is a disease with a very significant public health impact that has stubbornly resisted new therapies. Antibiotics are the only real therapeutic option, yet sepsis can be caused by over 100 bacteria and many fungi so a universal antibiotic is not a realistic option; the antibiotics and antifungals used have significant complications and are often unsuitable for fragile patients. The concept of cleansing the blood has been tried previously without success. Previous blood cleansing concepts have included laboratory scale methods of centrifugation, capillary electrophoresis, liquid chromatography, field flow fractionation, and liquid-liquid extraction. These devices have failed to deliver continuous flow cleansing devices. In additional to often discarding large portions of the blood, current cleansing devices may rely on: diluents, sheath flow, controlled solution conductivity, costly microfabricated on-chip materials, and toxic additives.

SUMMARY OF THE DISCLOSURE

According to one aspect of the disclosure, a blood cleansing device includes a microfluidic separation channel having an upstream portion and a downstream portion wherein the separation channel is shaped such that an interior portion of the upstream portion of the separation channel is substantially aligned with a wall of the downstream portion of the downstream portion of the separation channel. A width of the separation channel is between about 30% and 45% of a wavelength of a standing wave applied to the separation channel. Additionally, the separation channel includes a first inlet configured to introduce flowing whole blood into the upstream portion of the separation channel. The whole blood includes plasma, a plurality of formed elements and a plurality of undesirable particles. The separation channel also includes a first outlet positioned downstream from the first inlet and upstream from the downstream portion of the separation channel, a second outlet positioned within the downstream portion of the separation channel along the wall of the downstream portion that is aligned with the interior portion of the upstream portion of the separation channel, a second inlet positioned within the separation channel between the first outlet and the second outlet, and a third outlet positioned in the downstream portion of the separation channel downstream of the second outlet.

In some implementations, the width of the separation channel is between about 30% and about 35% or between about 35% and 45% of the wavelength of the standing wave applied to the separation channel. A thickness of the wall is between about 25% and about 45% of the wavelength of the standing wave applied to the separation channel.

In some implementations, the blood cleansing device includes at least a second separation channel and a third separation channel. The first outlet of the second separation channel is configured to carry fluid from the second separation channel to the second inlet of the separation channel, and the second inlet of the third separation channel is configured to receive fluid from the first outlet of the separation channel.

In some implementations, the blood cleansing device includes a microfluidic injector for introducing, into the separation channel, a plurality of lipid-based capture particles configured to bind to the undesirable particles. In some implementations, the microfluidic injector includes one of a microfluidic nozzle and a porous membrane coupled to a lipid reservoir. In other implementations, the separation channel is formed in a substrate comprising one of polystyrene, glass, and polyimide, acrylic, polysulfone, and silicon.

In other implementations, the blood cleansing device includes an acoustic transducer positioned adjacent to the separation channel and configured to impose a standing wave transverse to the length of the upstream portion of separation channel. The wave is configured to focus formed elements and a plurality of the undesirable particles bound to a plurality of capture agents towards an interior region of the upstream portion of the channel. Some implementations include a second acoustic transducer positioned adjacent the downstream portion of the separation channel and configured to impose a standing wave transverse to the length of the second portion of the separation channel. The wave from the second acoustic transducer is selected such that the formed elements will be driven away from the wall of downstream portion of the separation channel at a rate that is faster than a rate at which the wave drives the undesirable particles bound to the capture agents away from the wall.

In some implementations, the blood cleansing device includes a second outlet positioned sufficiently downstream within the downstream portion of the separation channel that in operation, a greater percentage of the undesirable particles that are bound to the capture agents flows out of the second outlet than out of the third outlet and a greater percentage of the formed elements flows out of the third outlet than out of the second outlet.

In some implementations, the upstream portion of the separation channel includes an aggregation point, and the upstream portion of the separation channel is configured such that a width of the first portion of the separation channel at the aggregation point is half the wavelength of the acoustic wave acting on the whole blood.

In other implementations, the separation channel includes walls having a thickness at a particle aggregation point that is a multiple of one quarter of the wavelength of an acoustic wave acting on the walls of the separation channel. In some implementations, the height of the separation channel at a particle aggregation point is less than one quarter of the wavelength of a standing acoustic wave acting on the particle aggregation point.

According to another aspect of the disclosure, a blood cleansing device includes a microfluidic separation channel having an upstream end and downstream end. The separation channel includes a first inlet configured to introduce flowing whole blood into a proximal end of the separation channel, the whole blood including plasma, a plurality of formed elements and a plurality of undesirable particles. A width of the separation channel is between about 30% and 45% of a wavelength of a standing wave applied to the separation channel. The separation channel also includes a first outlet at the downstream end of the separation channel positioned substantially along the longitudinal axis of the separation channel, a second outlet at the downstream end positioned adjacent a first wall of the separation channel, and a third outlet at the downstream end positioned adjacent a second wall of the separation channel, opposite the first wall. The device also includes an acoustic transducer positioned adjacent to the separation channel for imposing the standing acoustic wave transverse to a particle migration region of the separation channel, and a capture particle injector configured to introduce a plurality of lipid-based capture particles into the whole blood before the blood reaches the particle migration region of the separation channel.

In some implementations, the width of the separation channel is between about 30% and about 35% or between about 35% and 45% of the wavelength of the standing wave applied to the separation channel. A thickness of the wall is between about 25% and about 45% of the wavelength of the standing wave applied to the separation channel.

In some implementations, the device includes a reservoir in fluidic communication with the capture particle injector. In some implementations, reservoir contains a plurality of the lipid-based capture particles. In other implementations, the reservoir contains a mixture of materials, which when directed by the capture particle injector into the whole blood, form the lipid-based capture particles. In these implementations the materials in the mixture include an affinity molecule, a lipid, and a fluid with a density less than 1 g/cm$^3$. In some implementations, the affinity molecule is a glycoconjugate and/or lectin. In some implementations, the lipid-based capture particles have significantly different acoustophoretic mobility than that of formed elements of blood. In some implementations, the capture particle injector includes a microfluidic nozzle. In some implementations, the capture particle injector includes a porous membrane. In yet other implementations, the second and third outlets merge at a fourth outlet.

According to one aspect of the disclosure, a method of cleanings blood includes flowing whole blood, containing a plurality of undesirable particles, formed elements, and plasma, through a microfluidic separation channel. Then injecting capture particles, from a reservoir, into the separation channel such that the capture particles can bind to at least a plurality of the undesirable particles. A width of the separation channel is between about 30% and 45% of a wavelength of a first standing wave applied to the separation channel. Next, upstream of a first outlet of the separation channel, with the first standing acoustic wave, the whole blood and the captures particles are directed away from the walls of the separation channel. Then the method continues with directing, downstream of the first outlet and prior to a second outlet of the separation channel, the captures particles and the formed elements alongside a wall of the separation channel, and finally driving, prior to the second outlet, with a second standing acoustic wave, formed elements of the flowing whole blood away from the walls of the separation channel as the capture particles remain sufficiently close to the wall of the separation channel to flow out of the second outlet, while the formed elements flow out of a third outlet of the separation channel.

In some implementations, the width of the separation channel is between about 30% and about 35% or between about 35% and 45% of the wavelength of the first standing wave applied to the separation channel. A thickness of the wall is between about 25% and about 45% of the wavelength of the first standing wave applied to the separation channel.

In some implementations, the capture particles include affinity molecules anchored to a lipid bilayer encapsulating a fluid. In some implementations, the fluid has a density less than about 1 g/cm$^3$.

In some implementations, the affinity molecule, lipid, and fluid are mixed in the reservoir prior to their injection into the separation channel. In some of these implementations, injecting the capture particles includes injecting the mixture of the affinity molecule, lipid, and fluid through a nozzle such that the lipid forms a liposome surrounding the fluid. In some implementations, the capture particle includes a polystyrene bead. In yet other implementations, the capture particles have significantly different acoustophoretic mobility than that of formed elements of blood. In some implementations, the capture particles are less about 10 µm and greater than about 2 µm in diameter.

In some implementations, the formed elements of blood include at least one of red blood cells, white blood cells, and platelets. In some implementations, the method further includes unbinding the capture particles from the undesirable particles after flowing through the third outlet and introducing the unbound capture particles into the separation channel.

In other implementations, the formed elements are driven away from the walls at a faster rate than the capture particles and undesirable particles by the standing acoustic wave. In some implementations, the method further includes extracting whole blood from a patient prior to flowing the whole blood through the separation channel, the extracted whole blood having a first concentration of undesirable particles, and then reintroducing whole blood with fewer undesirable particles back into the patient after flowing whole blood through the plurality of microchannels.

According to another aspect of the disclosure, a method of cleansing blood includes flowing a suspension through a microfluidic separation channel. A width of the separation channel is between about 30% and 45% of a wavelength of a standing wave applied to the separation channel. The suspension includes a plurality of target particles having a positive acoustic contrast factor and a plurality of undesirable particles suspended in a fluid. The method also includes introducing, into the suspension, a plurality of positive contrast-factor capture particles selected to bind to the undesirable particles. The magnitude of the positive contrast-factor of the capture particles is substantially different than that of the target molecules. The method also includes applying the standing acoustic wave across the separation channel transverse to the direction of the flow of the suspension through the separation channel such that a pressure node forms along an interior axis of the separation channel, and collecting the positive-factor capture particles through an outlet of the separation channel at a distance along the separation channel that is sufficiently beyond the point in the channel at which the standing acoustic wave is introduced that the target particles are separated from the positive-factor capture particles.

According to another aspect of the disclosure, a method of cleansing blood includes flowing whole blood, including plasma, a plurality of formed elements, and a plurality of undesirable particles, into an inlet of a microfluidic separation channel. A width of the separation channel is between about 30% and 45% of a wavelength of the standing wave applied to the separation channel. The method includes introducing a plurality of lipid-based capture particles into the whole blood such that the lipid-based capture particles bind to a plurality of the undesirable particles. The standing acoustic wave is applied transverse to a direction of flow of the whole blood through the separation channel such that the formed elements aggregate to about the axial center of the separation channel and the capture particles aggregate along at least one wall of the separation channel. The method also includes collecting the formed elements of the whole blood at a first outlet positioned at a downstream end of the separation channel at about the axial center of the separation channel. Then the capture particles are collected through at least a second outlet positioned at the downstream end of the separation channel adjacent to the at least one wall along which the capture particles are aggregated.

In some implementations, the width of the separation channel is between about 30% and about 35% or between about 35% and 45% of the wavelength of the standing wave applied to the separation channel. A thickness of the wall is between about 25% and about 45% of the wavelength of the standing wave applied to the separation channel.

In some implementations, at least one wall includes at least one side wall of the separation channel, at least one of the top walls, and/or bottom walls of the separation channel. In some implementations, the capture particles comprise affinity molecules anchored to a lipid bilayer encapsulating a fluid. In some implementations, the fluid has a density less than 1 g/cm$^3$. In other implementations, the affinity molecule, lipid, and fluid are mixed in the reservoir prior to their injection into the separation channel. In some implementations, injecting the capture particles includes injecting the mixture of the affinity molecule, lipid, and fluid through a nozzle such that the lipid forms a liposome surrounding the fluid. In some implementations, the capture particle includes a polystyrene bead. In some implementations, the capture particles have significantly different acoustophoretic mobility than that of formed elements of blood. In some implementations, the capture particles are less than 5 μm or 2 μm in diameter. In some implementations, the formed elements of blood includes at least one of red blood cells, white blood cells, and platelets. In some implementations, the method further includes, extracting whole blood from a patient prior to flowing the whole blood through the separation channel, the extracted whole blood having a first concentration of undesirable particles, and reintroducing whole blood with fewer undesirable particles back into the patient after flowing whole blood through the plurality of microchannels.

According to another aspect of the disclosure, a method of cleansing blood includes flowing a suspension, which includes a plurality of target particles and a plurality of undesirable particles suspended in a fluid into an inlet of a microfluidic separation channel. A width of the separation channel is between about 30% and 45% of a wavelength of the standing wave applied to the separation channel. The method also includes introducing into the suspension a plurality of lipid-based capture particles such that the lipid-based capture particles bind to a plurality of the undesirable particles. The standing acoustic wave is applied transverse to a direction of flow of the suspension through the separation channel such that the target particles aggregate to about the axial center of the separation channel and the capture particles also aggregate along at least one wall of the separation channel.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIG. 7 is a cut away of a lipid-based capture particle, according to one illustrative embodiment;

FIGS. 8A-8E are illustrations of the components and use for a capture particle, as depicted in FIG. 7, according to one illustrative embodiment;

DETAILED DESCRIPTION OF THE PREFERRED EMBODIMENTS

The various concepts introduced above and discussed in greater detail below may be implemented in any of numerous ways, as the described concepts are not limited to any particular manner of implementation. Examples of specific implementations and applications are provided primarily for illustrative purposes.

The present system and methods described herein generally relates to a system for cleansing blood. Accordingly, in various implementations, the disclosure relates to the cleansing of whole blood by acoustically separating undesirable particles from the blood via high throughput microfluidic arrays. In certain implementations, in part to overcome the prior deficiencies with the poor performance of acoustic separation on small particles, prior to acoustic separation of the blood, capture particles are introduced and mixed with the blood to form complexes with the undesirable particles, yielding particles large enough to be effectively and efficiently targeted by acoustic separation.

Figure 1:
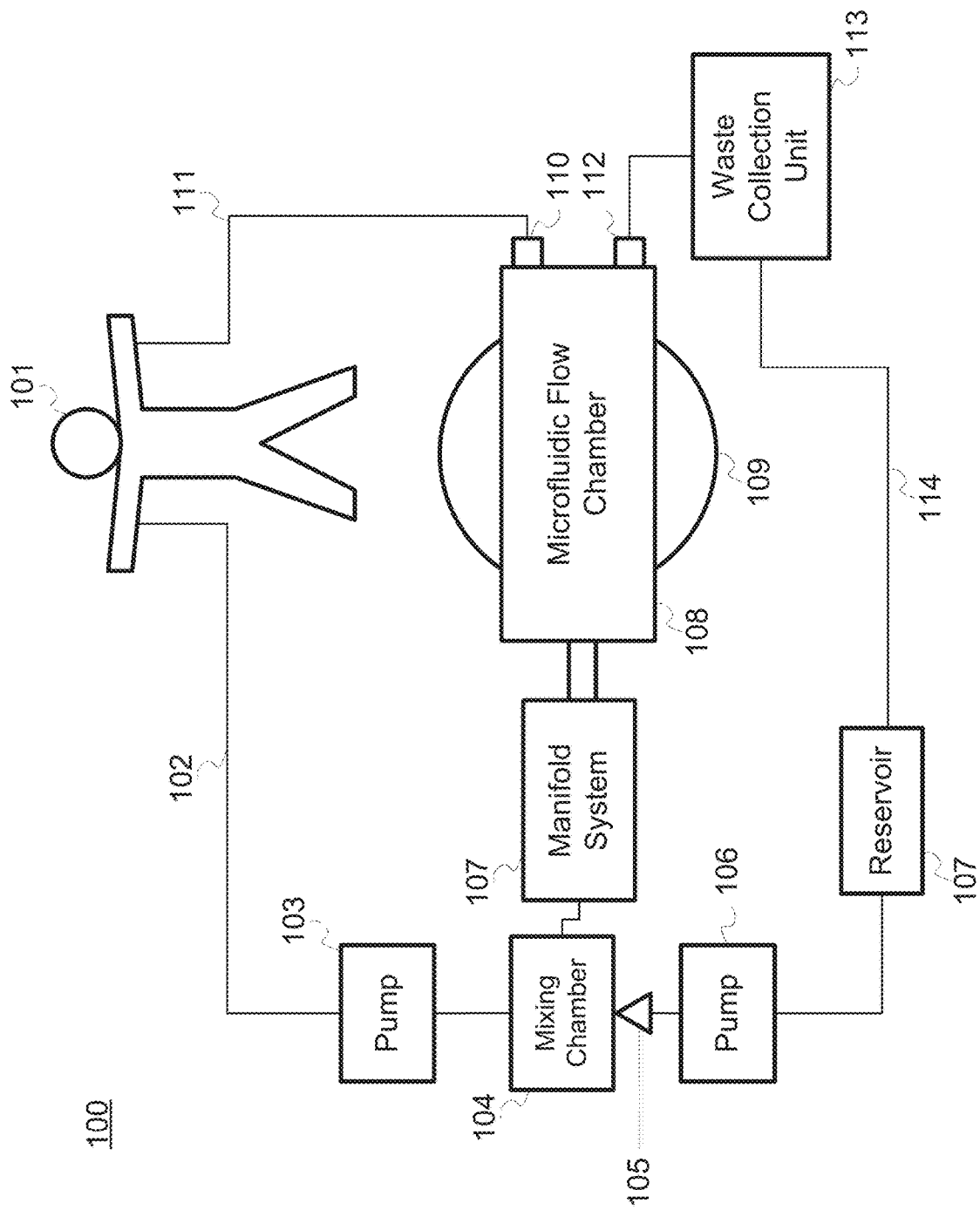
FIG. 1 is a block diagram of a system for cleansing blood, according to one illustrative embodiment.

FIG. 1 illustrates a system 100 for cleansing blood by removing waste material such as bacteria, viruses and toxins. In the system 100, blood is removed from a patient via an intravenous line 102. The blood is then pumped to a mixing chamber 104 by a first pump 103. In the mixing chamber 104, capture particles are mixed with whole blood. The components of the capture particles are stored in a reservoir 107. From the reservoir 107, the capture particles are pumped by a second pump 106 into the mixing chamber. The capture particles are formed as the contents of the reservoir 107 are extruded from a micronozzle 105 at the entrance to the mixing chamber 104. From the mixing chamber 104, the whole blood and capture particles enter a manifold system 107. The manifold system 107 distributes the whole blood and capture particles to a plurality of separation channels contained within the microfluidic flow chamber 108. The microfluidic flow chamber 108 sits atop at least one bulk piezoelectric acoustic transducer 109. The acoustic waves generated by the bulk piezoelectric acoustic transducers are used to funnel the contents of the whole blood and capture particles to specific outlets of the separation channels. As the whole blood flows through the microfluidic flow chamber 108, cleansed blood flows to a first outlet 110. After exiting the first outlet 100, the cleansed blood returns to the patient 101, via a second intravenous line 111. The capture particles and other waste material removed from the blood exit the microfluidic flow chamber 108 via a second outlet 112. Next, the waste material and capture particles enter a waste collection unit 113. In the waste collection unit 113, the capture particles are separated from the waste material. Once separated, the waste material is discarded and the capture particles are returned to the reservoir 107 by tubing 114. Once returned to the reservoir 107, the capture particles are reused in the system to remove additional waste material from whole blood as it continues to flow through the system.

The system 100, as illustrated, includes a pump 103 for moving blood from the patient 101 to the mixing chamber 104. In some implementations, the pump operates continuously, while in other implementations the pump works intermittently, and only activates when the level of whole blood in the mixing chamber 104 or manifold falls below a set threshold. In some implementations, the flow rate of the pump is configurable, such that the rate the blood exits the patient can be configured to be faster or slower than if no pump was used. In yet other implementations, no external pump is required. In this example, the blood is transported to the mixing chamber 104 by the pressure generated by the patient's own heart. In some implementations, the patient 101 is connected to a blood pressure monitor, which in turn controls the pump. Example pumps can include, but are not limited to, peristaltic pumps or any other pump suitable for flowing blood.

As illustrated in the system 100, capture particles are also pumped into the mixing chamber. A second pump 106 pumps the ingredients to form the capture particles from a reservoir 107 to the mixing chamber 104. In some implementations, the components of the capture particles are continuously agitated in the reservoir 107 in order to keep the components well mixed. The components are formed into capture particles as they enter the mixing chamber 104. The components enter the mixing chamber 104 through a micronozzle 105. In some implementations, the micronozzle 105 injects the capture particles into the mixing chamber 104. In other implementations, the micronozzle 105 injects the capture particles into the manifold system 107, and in yet other implementations the micronozzle 105 is positioned such that it injects capture particles directly into the separation channels of the microfluidic chamber 108. In some implementations, the micronozzle 105 is a micro-machined nozzle, configured to allow a specific amount of the capture particle components through the nozzle at a given time. In some implementations, the micronozzle is an array of micronozzles. In yet other implementations, the micronozzle is a membrane with pores. The pump 106 is configured to flow the contents of the reservoir through the micronozzle 105 at a predetermined rate such that the amphipathic characteristics of the molecules of the components of the captures particles cause the capture particles to spontaneously form as they exit the micronozzle 105.

In some implementations, a micronozzle is not used to generate the capture particles. In these implementations, the capture particles are premade. The capture particles are then stored in the reservoir and then introduced into the system by the pump 106 at either the mixing chamber 104, manifold system 107, and/or the separation channels of the microfluidic flow chamber 108.

As illustrated in system 100, the whole blood containing undesirable particles and the capture particles enter the mixing chamber 104. In some implantations, the contents of the mixing chamber are continuously agitated to improve distribution of the capture particles throughout the whole blood and undesirable particles such that the capture particles bind to the undesirable particles. In some implementations, anticoagulants or blood thinners are introduced into the mixing chamber 104 to assist the blood as it flows through the system 100. In some implementations, the mixing chamber 104 contains a heating element for warming the contents of the mixing chamber 104.

The contents of the mixing chamber 104 then flow into the manifold system 107, as illustrated by system 100. The manifold system 107 flows the whole blood, undesirable particles, and capture particles into the inlets of the plurality of separation channels of the microfluidic flow chamber 108.

In the illustrated system 100, the microfluidic flow chamber 108 contains a plurality of separation channels. The capture particles and undesirable particles are driven with standing acoustic waves to outlets. In some implementations, the separation occurs during a single stage, while in other implementations, the separation occurs over a plurality of stages. In some implementations, the microfluidic flow chamber is disposable.

As show in the illustrations of system 100, the microfluidic flow chamber 108 sits atop a bulk piezoelectric acoustic transducer 109. In some implementations, the system 100 contains a single bulk piezoelectric acoustic transducer 109, while in other implementations the system 100 contains a plurality of bulk piezoelectric acoustic transducers 109.

In some implementations, the bulk piezoelectric acoustic transducer 109 is glued to the microfluidic flow chamber 108. In other implementations the microfluidic flow chamber 108 is clamped to the bulk piezoelectric acoustic transducer 109 so the microfluidic flow chamber may easily be removed from the system. In other implementations the adhesive material connecting the bulk piezoelectric acoustic transducer 109 to the microfluidic flow chamber 108 is removable, for example by heating the adhesive.

The bulk piezoelectric acoustic transducer 109 imposes a standing acoustic wave on the separation channels of the microfluidic flow chamber 108 transverse to the flow of the fluid within the microfluidic flow chamber 108. The standing acoustic waves are used to drive fluid constituents towards or away from the walls of the separation channels or other aggregation axes.

More particularly, the dimensions of the separation channels are selected based on the wavelength of the imposed standing wave such a pressure node exists at about the center or other interior axis of the separating channel, while antinodes exists at about the walls of the separation channel. Particles are driven to different positions within the channel based on the sign of their acoustic contrast factor at a rate which is proportional to the magnitude of their contrast factor. Particles with a positive contrast factor (e.g. the formed elements of blood) are driven towards the pressure node within the interior of the separation channel. In contrast, particles with a negative contrast factor are driven toward the pressure antinodes. These principles are depicted and described further in relation to FIGS. 5A and 5B.

Based on these principles, formed elements of blood can be separated from capture particles (and thus the undesirable particles bound to the capture particles) in two ways. In one way, as described further in relation to FIGS. 2 and 10, capture particles are selected to have negative contrast factors, which is opposite to the positive contrast factors of the formed elements of blood. Thus, in response to the standing acoustic wave, the formed elements are driven towards the resulting pressure node while the capture particles are driven towards the antinodes.

This technique can be used in a single-stage separation system. As whole blood, undesirable particles and capture particles mix in the mixing chamber 104 and continue to mix as flowing through the manifold system 107, the capture particles bind to the undesirable particles. As the whole blood, undesirable particles and capture particles enter the area of the separation channel where the standing acoustic wave is imparted, the standing acoustic wave drives the capture particles and bound undesirable particles to a specific axis (e.g., against the wall of the separation channel) and the formed elements of the whole blood to a second axis (e.g., the middle of the separation channel). Thus, the capture particles and undesirable particles can be collected from the edges of the separation channel and disposed of while the cleaned blood is collected and returned to the patient.

Alternatively, capture particles can be separated from formed elements of blood based on a time of flight principle. That is, if the capture particles are selected to have a contrast factor that is the same sign as that of the formed elements of blood, but with a substantially different magnitude, and assuming the formed elements and capture particles are substantially aligned prior to the application of a standing wave at a distance away from the positive pressure node induced by the wave, the formed elements and capture particles will migrate towards the pressure node at different rates. Thus, the formed elements and capture particles can be collected separately at a point where the higher contrast factor particles (capture particles or formed elements depending on the selected capture particles) have move sufficiently far from the initial aggregation axis that they have separated from the capture particles due to their difference in acoustophoretic mobility. Thus, in some implementations, a two-stage separation process is employed. In the two-stage process, formed elements of blood and capture particles are first aggregated along a common first axis of the separation channel using a first standing acoustic wave. Then after they have reached the common aggregation axis, a second standing acoustic wave drives the formed elements and capture particles to a second aggregation axis. However, instead of waiting until the formed elements and capture particles all reach the second aggregation axis, the channel splits to direct the particles having the lower acoustophoretic mobility down a first outlet. The particles that have a greater acoustophoretic mobility, which would have already migrated towards the second aggregation axis to a point that they are beyond entrance to the first outlet, flow out a second outlet. This separation technique is described further in relation to FIGS. 3 and 10.

As illustrated in the system 100, the cleansed blood exits the microfluidic flow chamber 108 at a first outlet 110. From there the blood is returned to the patient 101 via an intravenous supply line 111. In some implementations, the blood in the supply line 111 is reheated to body temperature before returning to the patient 101. In other implementations an infusion pump is used to return the blood to the patient 101, while in the system 100 the pressure generated in the system by pumps 103 and 106 is adequate to force the blood to return to the patient 101.

As illustrated in the system 100, waste material (e.g. the capture particle and undesirable particles) exit the microfluidic flow chamber 108 and enter a waste collection unit 113. In some implementations, the waste collection unit 113 contains a capture particle recycler. The capture particle recycler unbinds the undesirable particles from the capture particles. The capture particles are then returned to the reservoir 107 via tubing 114. The undesirable particles are then disposed of. In some implementations, the undesirable particles are saved for further testing.

While the system 100 is described above for the in-line cleansing of a patient's blood, in alternative implementations, the system 100 can be used to cleanse stored blood. For example, the system 100 can be used to cleanse collected blood for later infusion to help ensure the safety of the blood.

Figure 2:
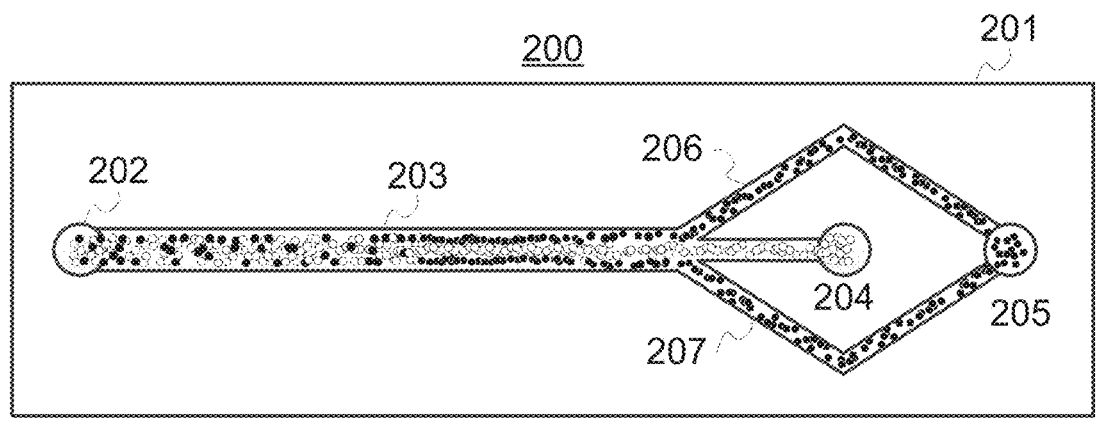
FIG. 2 is a top view of a single-stage separation channel, such as can be used in the system of FIG. 1, according to one illustrative embodiment.

FIG. 2 illustrates an example single-stage separation channel suitable for use within the microfluidic flow chamber 108 of the blood cleansing system 100. The separation channel includes an inlet 202, a flow channel 203, a first outlet 204, a first outlet channel 206, a second outlet channel 207, and a second outlet 205. The separation channel is manufactured in a sheet of material 201.

In FIG. 2, whole blood, undesirable particles, and capture particles enter the separation channel at the inlet 202 from the manifold system 107. The whole blood, undesirable particles, and capture particles then flow the length of the flow channel 203. The flow channel is subdivided into three regions: an upstream region, a downstream region, and a migration region. The migration region lies between the upstream and downstream regions, and is the region of the flow channel where the standing acoustic wave is imparted transverse to the flow of particles. As the formed elements of the whole blood, capture particles and the undesirable particles enter the migration region, the standing acoustic wave drives the capture particles bound to the undesirable particles to the side walls of the separation channel, and the formed elements of the whole blood to the center of the channel. The formed elements of the whole blood then exit the separation channel through the outlet 204 located at about the central axis of the separation channel. The capture particles and undesirable particles then exit the separation channel through the first and second outlet channels 206 and 207 which terminates in the second outlet 205. In some implementations, the formed elements are driven to the walls of the separation channel and the capture and undesirable particles remain in the center of the separation channel.

In some implementations, the separation channel 200 can separate undesirable particles from any fluid. As discussed above and later in relation to FIGS. 5 and 7, the separation channel 200 can be used to remove undesirable particles from any fluid, so long as the characteristics of the capture particle are appropriately selected. For example, selecting an encapsulated fluid such that its density and bulk modulus gives the capture particle a contrast factor that distinguishes it from the fluid and other particles in the fluid. For example, the separation channel 200 may be used to remove undesirable particles from, but not limited to, blood plasma, blood serum, water, liquid food products (e.g., milk), and lymph.

In the implementation of FIG. 2, the outlet 205 is formed from the merging of two outlet channels 206 and 207. In some implementations, the streams do not rejoin, but lead to separate outlet terminals.

In FIG. 2, the particles are separated in the same plane as the sheet of material 201 (i.e. particles are aligned to the left, right, or center of the channel); however, in other implementations, the particles are separated out of plane. For example, in some implementations, the particles are aligned with the top, middle, or bottom of the channel.

In FIG. 2, the sheet of material 201 can include, but is not limited to, polystyrene, glass, polyimide, acrylic, polysulfone, and silicon. The channel can be manufactured by a number of manufacturing techniques, including, but not limited to, milling, embossing, and etching.

In some implementations, a higher frequency standing acoustic wave can be applied to create two pressure nodes within the separation channel 200, both spaced apart from the sidewalls of the channel and separated by an anti-node. In one such implementation, the formed elements in the blood aggregate into two substantially parallel streams near the sidewalls along the pressure nodes, while the capture particles migrate to the center of the channel in line with the anti-node. In such implementations, the capture particles exit the separation channel through the outlet 204, while the blood exits the separation channel through the first and second outlet channels 206 and 207.

Figure 3:
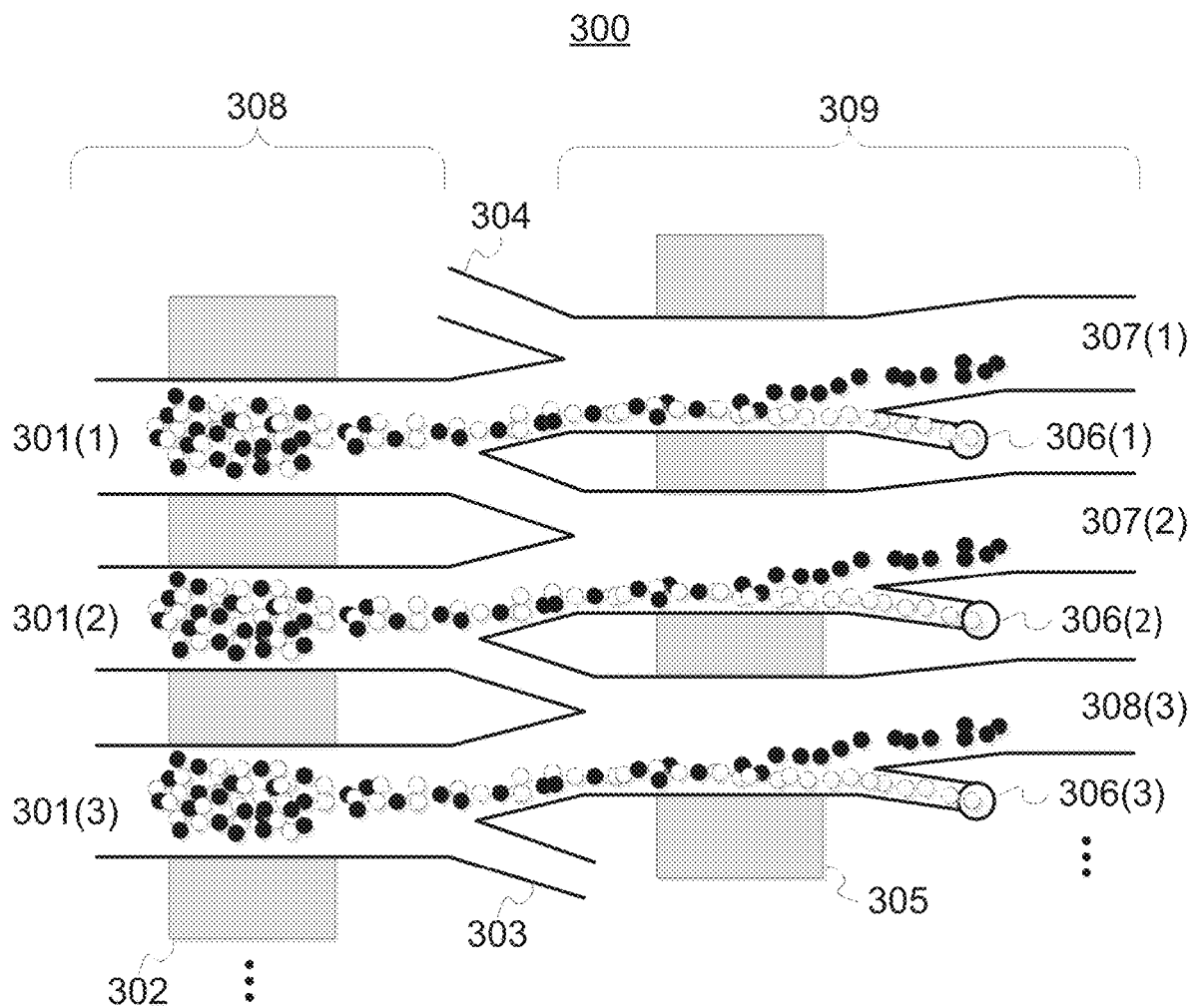
FIG. 3 is a top view of a network of two-stage separation channels, such as can be used in FIG. 1, according to one illustrative embodiment.

FIG. 3 illustrates an example network 300 of multistage separation channels suitable for use the blood cleansing system 100 depicted in FIG. 1. The network of separation channels includes a plurality of first inlets 301. FIG. 3 also includes first and second acoustic bulk transducers 302 and 305, respectively. Additionally, each separation channel includes an upstream outlet 303 and a second inlet 304. The upstream outlet 303 of each channel is connected to the second inlet 304 of its neighboring channel. The fluid exits the separation channels through a first downstream outlet 307 or second downstream outlet 306.

In each separation channel of the network 300, the flow channel through which most of the fluid in the channel flows shifts after the upstream outlet 303. The portion of the separation channel prior to the shift is referred to as the upstream portion 308 and the portion after the shift is referred to as the downstream portion 309. As the particles within the blood continue to flow down the separation channel, one subset of particles is driven into a first downstream outlet 307 and a second subset of the particles are driven into a second downstream outlet 306. For example, the cleaned blood exits through the first downstream outlet 307 and the capture particles with bound undesirable particles exits through the second downstream outlet 306.

As described above, and illustrated in FIG. 3, the separation channels in the network 300 are generally divided into upstream portions 308 and downstream portions 309. The two portions are distinguished by a shift in the separation channel. The angle of the shift is referred to as the branching angle. The branching angle for a particular implementation is chosen to substantially align a wall of the downstream portion 309 with an interior axis of the upstream portion 308. The selected axis corresponds to the location of a pressure node induced in the channel by the first acoustic transducer 302. For example, in some implementations, a wall of the downstream portion 309 is configured to align with an interior axis substantially in the middle of the upstream portion 308.

In the illustration of FIG. 3, there are a plurality of first inlets 301. The number of first inlets, and thus separation channels, can be increased to n where n is the number of separation channels required to meet the flow demands of a specific implementation. In some implementations, the first inlets 301 are configured to accept flowing whole blood and a plurality of capture particles. The flowing whole blood includes plasma, a plurality of formed elements and a plurality of undesirable particles. The formed elements of blood can include leukocytes (white blood cells), erythrocytes (red blood cells), and thrombocytes (platelets). In some implementations, the capture particles begin binding to the undesirable particles as they are mixed as they flow down the length of the upstream portion 308. In other implementations, the capture particles are mixed with the whole blood prior to flowing through the first inlet 301, and thus the binding of the capture particles and undesirable particles can begin before the blood is flowed through the first inlet 301.

As the fluid in the separation channels flows downstream it passes over a first bulk acoustic transducer 302 and eventually a second bulk acoustic transducer 305. The bulk acoustic transducers 302 and 305 impart standing acoustic waves on the separation channels. The standing acoustic waves are transverse to the flow of fluid through the separation channels. In some implementations, the acoustic bulk transducers 302 and 305 emit standing acoustic waves of different wavelengths. In other implementations the acoustic bulk transducers 302 and 305 emit standing acoustic waves of the same wavelength. Example acoustic waves can have, but are not limited to, wavelengths between about 1 and about 4 MHz.

In the network 300, the first acoustic bulk 302 transducer aligns the formed elements, capture particles, and undesirable particles in the interior of the upstream portions 308 of the separation channels. After the particles in the fluid are aligned in the middle of the flow channels, the channels angle to align the particles with walls of the downstream portions 309. With all particles aligned in the middle of the flow channel, fluid substantially away from the middle is free of capture particles and undesirable particles. Thus, at the angle in the flow channels, a portion of the fluid, substantially void of formed elements, capture particles and undesirable particles, exits through the upstream outlets 303. The particles continue to flow downstream, now substantially aligned with a wall of the respective downstream portions 309. Fluid entering the downstream portions 309 of the separation channels from the second inlets 304 ensures continued flow of the formed elements and capture particles through the downstream portions of the 309 of the separation channels.

In the second stage particles are separated based on the speed at which (and thus distance) they travel from a given aggregation axis towards a second pressure node induced in the channel by a second standing acoustic wave. As indicated above, due to the angling of the separation channels, the formed elements and capture particles enter the downstream portions of the separation channels aggregated along one wall.

As the particles flow along the wall of the separation flow channels, they pass over a second bulk transducer 305, which emits a second standing acoustic wave transverse to the flow of the particles. The second standing acoustic wave drives the particles away from the wall. Based on the magnitude of their contrast factor, a first subset of particles (e.g., the formed elements of blood) moves away from the wall at a faster rate then a second subset of particles (e.g., the capture particles).

This differential rate of movement is achieved by using capture particles that have an acoustophoretic mobility that is substantially different from that of the formed elements of blood. The different acoustophoretic mobility is in turn based on the magnitude of the contrast factor of capture particles being substantially different from the magnitude of the contrast factor of the formed elements of blood. The speed at which the two groups move away from the wall can be calculated, and the rate of flow of blood through the system is known. Thus, the distance the formed elements will be moved away from the wall of a separation channel at a given location after being exposed to the second acoustic standing wave can also be calculated. This distance is termed d(f, x), where d is the distance traveled away from the wall given a specific fluid flow rate (f) and a specific distance (x) after the application of the standing acoustic wave. Based on this calculation, the separation channel can be divided into two outlets. The second downstream outlet 306 is positioned along the wall the formed elements and capture particles were previously flowing. The second downstream outlet 306 is constructed to have a width just smaller than d(f, x). Thus, the formed elements, having traveled a distance of d(f, x) away from the wall due to the second standing acoustic wave would have been driven beyond the second outlet by the time they reach the distance (x), and thus are driven into the first downstream outlet 307. In contrast, the capture particles bound to the undesirable particles, having traveled a distance substantially less than d(f, x) due to their lesser acoustophoretic mobility, remain substantially near the wall of the downstream portion 309 and exit the second outlet 306. In some implementations, the distance (x) traveled between exposure to the standing acoustic wave and entering the first downstream outlet 307 is between about 1 and about 10 cm.

Figure 4:
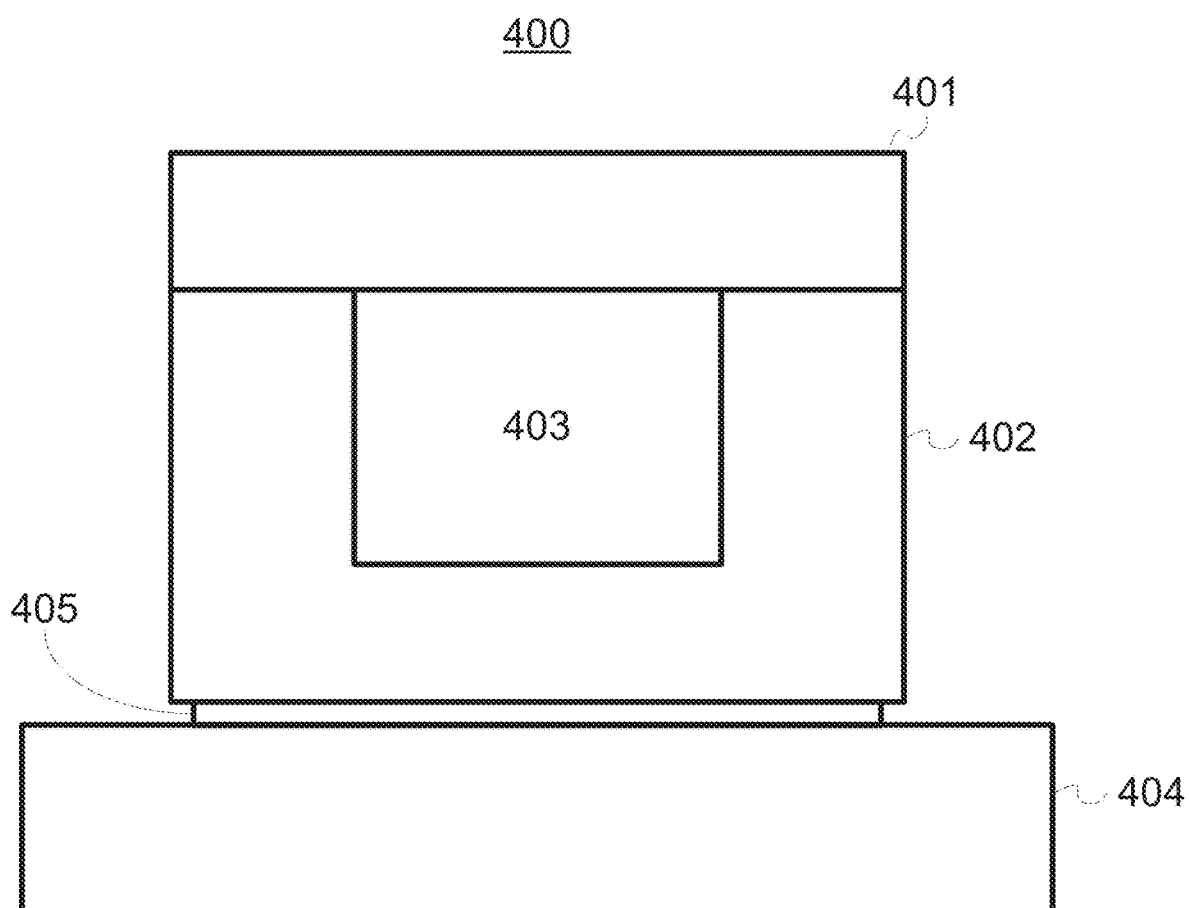
FIG. 4 is a cross sectional view of a single-stage separation channel, such as the separation channel of FIG. 2, mounted to a bulk transducer, according to one illustrative embodiment.

FIG. 4 is an illustrative cross-section of a separation channel 400 similar to the separation channel depicted in FIG. 2. The separation channel 400 includes a top layer 401 sitting atop a bottom layer 402. A channel is created in the bottom layer 402. When the top layer 401 is placed on the bottom layer 402 a lumen 403 is created. The separation channel 400 sits atop a bulk piezoelectric transducer 404. The separation channel 400 is secured to the bulk transducer 404, by a coupling adhesive 405 and/or mechanical clamp. In some implementations, the coupling adhesive is cyanoacrylate glue.

The bottom layer 402 and top layer 401 of the separation channel 400 are manufactured from a substrate sheet. The substrate sheet can be made of, without limitation, polystyrene, glass and polyimide, polyacrylic, polysulfone, and silicon. In some implementations, the bottom layer 402 is manufactured by milling, embossing, and/or etching. After creating the two layers, they can be joined together by thermacompression, mechanical clamping, adhesive bonding, and/or plasma bonding. As described above, the separation channel sits atop an acoustic bulk transducer 404. The transducer 404 imparts a standing acoustic wave of a specific wavelength ($\lambda$) across the channel. The dimensions of the bottom layer 402, top layer 401, and lumen 403 are dependent on the selected wavelength. In some implementations, the dimensions of the bottom layer 402, top layer 401, and lumen 403 are dependent on the selected wavelength and the material used to manufacture the substrate sheet. For example, for substrates formed from glass and some plastics, the width of the lumen 403 is equal to about half the wavelength ($\lambda_{fluid}/2$) of the acoustic wave in the fluid. The thickness of the side wall is equal to about a multiple of one quarter of the wavelength ($n \times \lambda_{wall}/4$) of the acoustic wave in the solid channel wall. The height of the lumen is preferably less than one quarter of the wavelength ($<\lambda_{fluid}/4$) of the acoustic wave in the fluid, and the thickness of the top layer 401 can be arbitrarily selected; however, in some implementations is chosen to be greater than one quarter of the wavelength ($>\lambda_{wall}/4$) of the acoustic wave in the solid channel wall.

In some other implementations, the bottom layer 402, top layer 401, and lumen 403 can have different relative dimensions when different materials are used for the manufacture of the substrate sheet. For example, for separation channels 400 formed from a thermoplastic, such as polystyrene, polyimide, polyacrylic, or polysulfone, the width of the lumen 403 in the bottom layer 402 is less than the one-half the wavelength of the acoustic wave in the fluid. In some implementations to focus the particles in about the center of the lumen, the width of the lumen 403 in a thermoplastic separation channel 400 is between about 25% and about 45%, about 30% and about 40%, or about 30% and about 35% of the wavelength of the acoustic wave in the fluid. The shorter width results from the smaller impedance mismatch between the thermoplastic walls of the separation channel and the fluid passed through the channel. This lower mismatch provides imperfect acoustic reflection, thereby motivating the narrower channel. Particularly in comparison to glass or silicon-based separation channels, thermoplastic separation channels are substantially less expensive to manufacture. In some implementations, when using a thermoplastic, the width of the wall is selected to be between about 35% and about 70%, about 35% and about 50%, about 35% and about 45%, or between about 40% and 45% of the wavelength of the acoustic wave in the fluid.

In one implementation, a separation channel formed from polystyrene can operate with an acoustic wave having a frequency of about 1.0 MHz. Assuming the channel is configured for carrying water, the lumen of the separation channel may be about 0.4 mm wide, or about 40% narrower than half the wavelength of the wave. Moreover, the sidewalls of the bottom layer 402 of a thermoplastic-based separation channel may be significantly wider than sidewalls formed from materials that serve as better acoustic reflectors. Table 1 below includes additional experimental data showing sample thermoplastic separation channel dimensions and excitation frequencies appropriate for carrying either Human Whole Blood (HWB) mixed with Phosphate buffered saline (PBS) or 4.4 micron polystyrene (PS) beads suspended in isopropyl alcohol (IPA) at a flow rate of about 100 μL/min. In each of the experiments used to create the below table, the top wall was 800 μm thick and the bottom wall was 1000 μm thick. The data set forth in Table 1 is illustrative in nature only, and is not intended to narrow the scope of the disclosure included herein.

TABLE 1

| | | | | | | |
|---|---|---|---|---|---|---|
| Channel Width [mm]: | 0.43 | 0.43 | 0.53 | 0.53 | 0.33 | 0.97 |
| Wall Width [mm]: | 1.05 | 1.05 | 1 | 1 | 1.1 | 0.78 |
| Device Width [mm]: | 2.53 | 2.53 | 2.53 | 2.53 | 2.53 | 2.53 |
| Channel Height [mm]: | 0.2 | 0.2 | 0.2 | 0.2 | 0.2 | 0.2 |
| Fluid: | 20% HWB in PBS | 4.4 µm PS beads in IPA | 4.4 µm PS beads in IPA | 20% HWB in PBS | 10% HWB in PBS | 10% HWB in PBS |
| Frequency Range Tested [MHz]: | 0.985-1.9 | 0.985-1.8 | 0.66-2.08 | 0.66-2.08 | 0.65-1.8 | 0.68-1.85 |
| Primary, Single-Band Focusing Frequency [MHz] | 1.015 | 1.033 | 0.92 | 0.63 | 1.55 | N/A |
| Primary, Dual-Band Focusing Frequency [MHz] | 1.7227 | 1.76 | 1.64 | 1.67 | N/A | 1.03 |
| Channel width as percentage of wavelength in fluid [%] | 30 | 39 | 42 | 23 | 34 | |
| Wall width as percentage of wavelength in wall material [%] | 45 | 45 | 38 | 26 | 71 | |

Figure 5A:
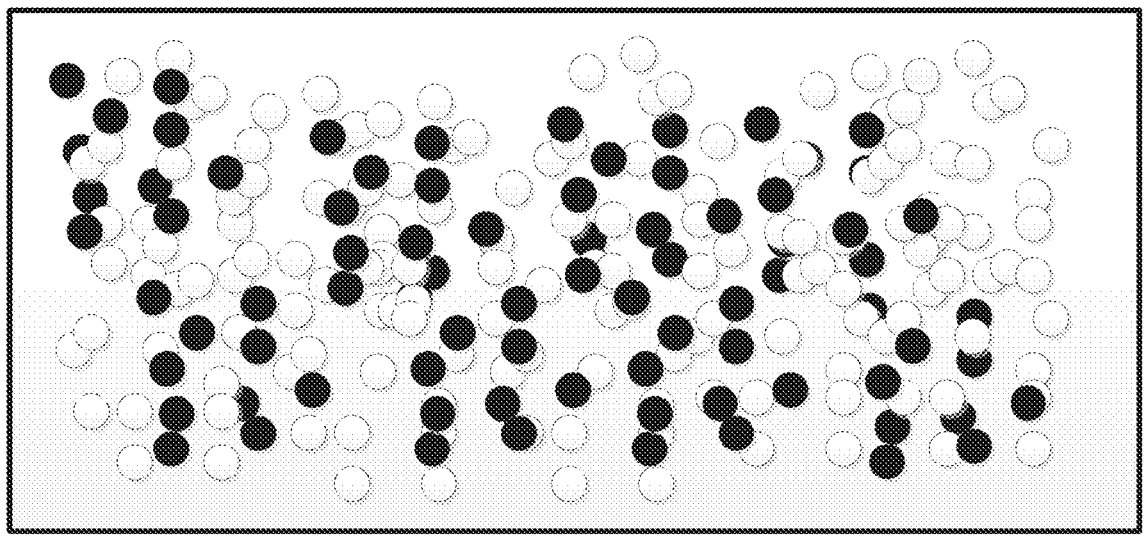
FIG. 5A is a cross sectional view a single-stage separation channel, as depicted in FIG. 2, containing a plurality of particles lacking an active acoustic transducer, according to one illustrative embodiment.
Figure 5B:
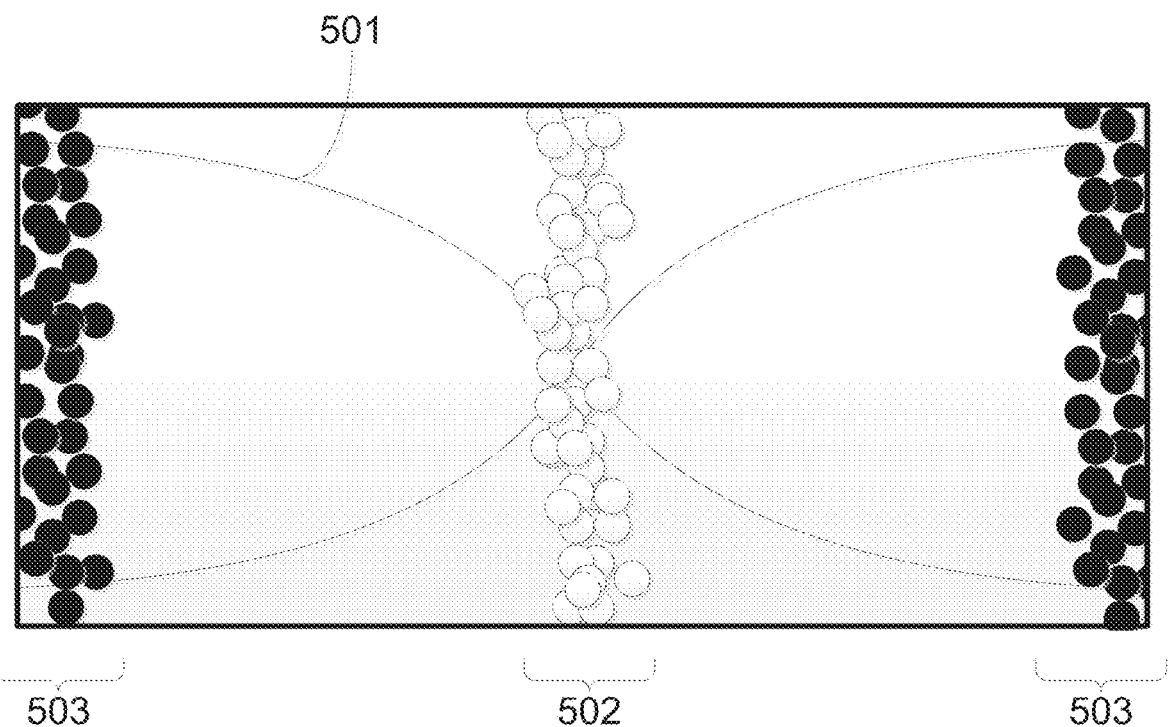
FIG. 5B is a cross sectional of a single-stage separation channel, as depicted in FIG. 2, containing a plurality of particles adjacent to an active acoustic transducer, according to one illustrative embodiment.

FIGS. 5A and 5B are cross sectional views of particles suspended in a fluid as they flow through a separation channel similar to the separation channel 200. For FIGS. 5A and 5B, the flow of the fluid is transverse to the plane of the drawings. In some implementations, the fluid is whole blood, and the particles are the formed elements and capture particles. For illustrative purposes, FIGS. 5A and 5B contains two particles, red blood cells (white dots) and capture particles (black dots). FIG. 5A illustrates blood flowing through a channel without a standing acoustic wave being imparted on the channel and its contents. In FIG. 5A, the particles remain homogenously mixed throughout the channel. In FIG. 5B, a standing wave is imparted on the channel. The standing acoustic wave 501 creates two node types. A pressure node occurs at 502. The node extends across the full height of the lumen. The channel dimensions set forth above in relation to FIG. 4 yield a pressure node at approximately the center of the channel.

Particles are aligned based on the sign of their contrast factor. Particles with a positive contrast factor (e.g. the formed elements of blood) are driven towards a pressure node 502. In contrast, particles with a negative contrast factor (e.g. capture particles used in the single-stage device described above) are driven toward the pressure antinodes 503.

Figure 6A:
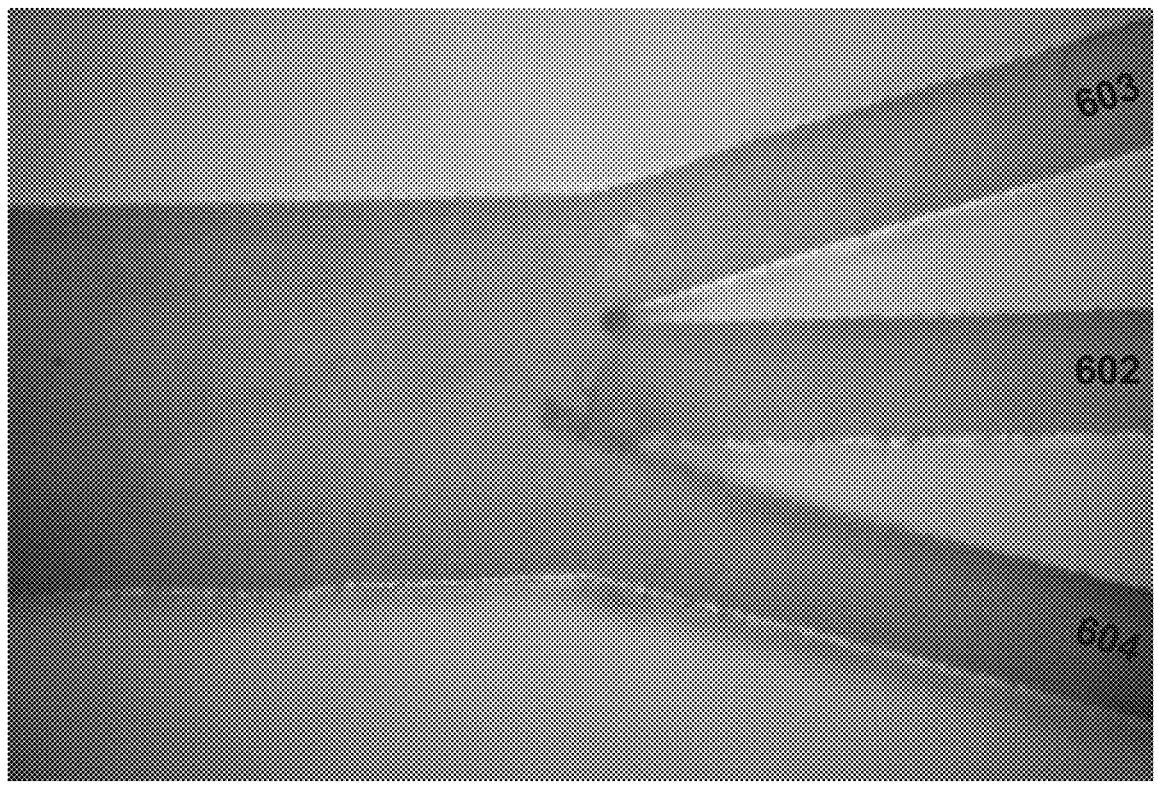
FIG. 6A is a top view of a separation channel, as depicted in FIG. 2, in which fluid is flown through the channel without the application of the standing acoustic wave.

FIG. 6A is a top view of a separation channel 600, as depicted in FIG. 2, in which fluid is flown through the separation channel 600 without the application of the standing acoustic wave. The separation channel 600 includes three outlets 602, 603 and 604. As with FIG. 5A, particles suspended in the fluid are homogeneously distributed throughout the fluid, and thus are not readily discernible in the image. The particles flow substantially evenly out of all three outlets 602, 603 and 604.

Figure 6B:
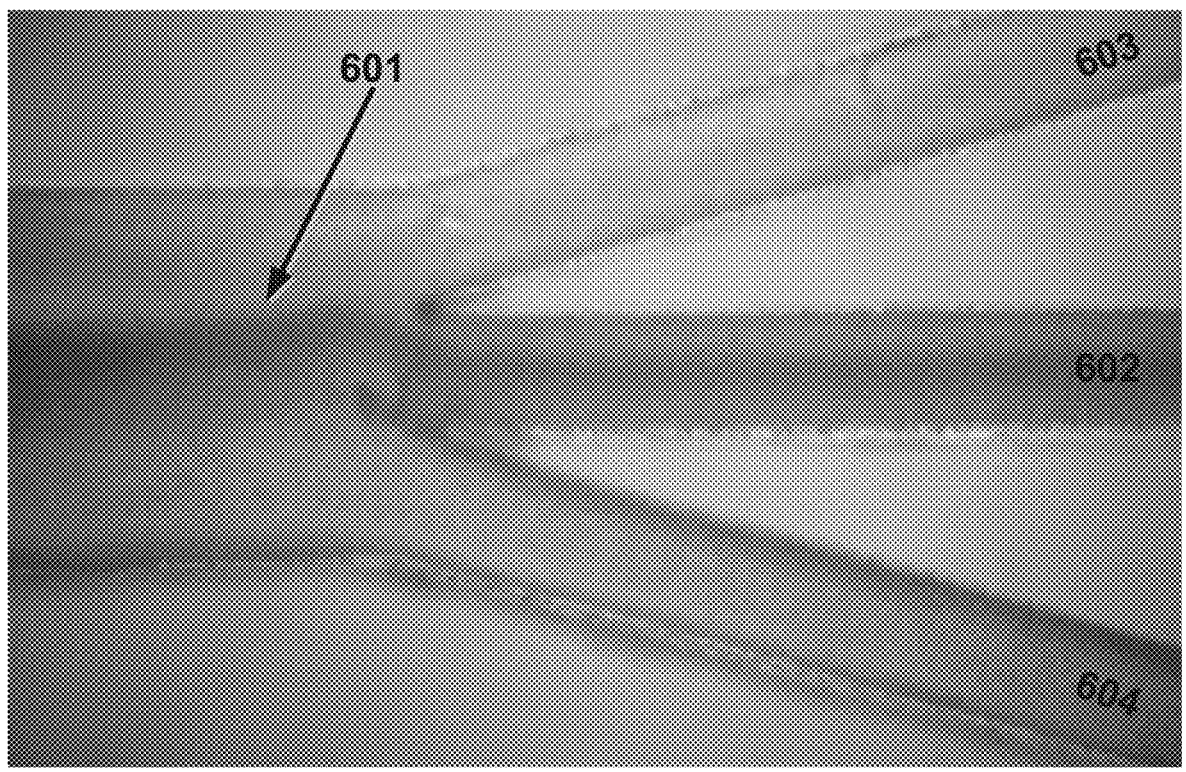
FIG. 6B is a top view of a separation channel, as depicted in FIG. 2, after the application of a standing acoustic wave, according to one illustrative embodiment.

In contrast, FIG. 6B is a top view of the separation channel 600, as depicted in FIG. 2, after the application of a standing acoustic wave, according to one illustrative embodiment.

In FIG. 6B, as a result of the standing acoustic wave, the particles 601 suspended in the fluid are aligned with the middle of the separation channel 600. Once aligned with the middle of the separation channel 600, the particles 601 exit the separation channel 600 through the middle outlet 602. The remaining fluid, substantially devoid of particles, exits the separation channel through the side outlets 603 and 604.

FIG. 7 is an illustrative example of a lipid bilayer capture particle 700. The capture particle 700 includes a lipid bilayer 701 encapsulating a fluid 702. Anchored in the lipid bilayer are affinity particles 703. The affinity particles bind and capture undesirable particles 704.

More specifically, the lipid bilayer 701 forms a liposomal capture particle. In some implementations, the lipids may be, but are not limited to dilauroyl-glycero-phosphoglycerol and dilauroyl-glycero-phosphocholine. The capture particle is tuned for acoustically induced mobility. Entities that differ in size, density, and/or compressibility have the greatest differential mobility in acoustic fields and thus are the most readily separable. Therefore, in some implementations, the size, density, and/or compressibility of the capture particles is modified to distinguish the capture particle from the formed elements of blood. The acoustic mobility of a particle is proportional to its volume. For example, in some implementations, the capture particles are about 1 µm in diameter. In other implementations they are between about 2 and about 5 µm in diameter. In some other implementations, the capture particles are between about 10 and about 20 µm in diameter. In some implementations, use of such larger capture particles results in a more distinct separation between the capture particles and red blood cells.

In implementations that adjust the compressibility of the capture particle, the rigidity of the capture particle can be adjusted by controlling the lipid components in the bilayer. The length and saturation of the lipid hydrocarbon tail, cross-linking of the hydrophobic domains, and/or the inclusion of cholesterol can all affect the fluidity and compressibility of a liposome.

In other implementations, the density of the liposome is engineered by encapsulating an acoustically active fluid 702. In these implementations the acoustical active molecule can be a FDA-approved contrast agent, glycerine, castor oil, coconut oil, paraffin, air, and/or silicone oil. In other implementations, all the above described characteristics are manipulated to create a capture particle with the greatest possible difference in contrast factor compared to a formed element.

As described above, the acoustically induced mobility of a particle is based on the contrast factor of the particle. For a liposomal based capture particle, the contrast factor is dominated by the properties of the encapsulated fluid. The contrast factor is based on the bulk modulus (K) and density (ρ) of the encapsulated fluid. When suspended in blood, the contrast factor (φ) for a capture particle, encapsulating a specific fluid, is calculated with the below equation:

$$\varphi = \frac{5\rho - 2 \cdot 1.02}{2\rho + 1.02} + \frac{2.2}{K}$$

Table 2 provides the ρ, K, and then calculated φ-factor based on the above equation.

TABLE 2

Calculated Contrast Factors

|  | Materials | ρ (g/ml) | K(Gpa) | φ |
|---|---|---|---|---|
| Encapsulated Fluids | glycerine | 1.25 | 4.7 | +0.73 |
|  | castor oil | 1.03 | 2.06 | −0.06 |
|  | coconut oil | 0.92 | 1.75 | −0.36 |
|  | paraffin | 0.80 | 1.66 | −0.58 |
|  | silicone oil | 1.04 | 1.09 | −1.00 |
|  | air | 0.002 | 1.4 | −3.55 |
| Formed Elements | white blood cell | 1.02 | 2.5 | +0.12 |
|  | red blood cell | 1.10 | 3.0 | +0.34 |

In some implementations, such as the implementation of FIG. 3, the capture particles have a contrast factor that is lower in magnitude, but still of the same sign as the formed elements. In these implementations, the low contrast factor of the capture particles can be achieved by making the capture particles sufficiently small to reduce their contrast factor to below that of the formed elements.

As illustrated in FIG. 7, affinity molecules 703 are embedded in the lipid bilayer 701. In some implementations, these affinity molecules are glycoconjugates. The glycoconjugates enable the capture and retention of all major classes of pathogens, including bacteria and viruses. In some implementations, the affinity molecules 703 also bind to toxins and pro-inflammatory cytokines. In some implementations, affinity molecules 703 are designed to universally capture gram-negative and gram-positive bacteria, virus, toxins, by exploiting that: 1) pathogens express unusual surface N- and O-linked glycan structures that can be targeted by glycan-binding proteins or lectins and 2) many pathogens and toxins bind to charged polysaccharides, especially those of the heparan sulfate family, that are present on the cell surface of mammalian cells. Some implementations employ glycoconjugate capture agents that have two components: a modified, non-anticoagulant heparin fragment that nevertheless maintains high affinity, multivalent binding properties, and a glycan-binding protein that binds to surface N- and O-linked glycans present on the surface of pathogens. In other implementations, the glycan structure is a lectin. For example the lectin can be, but is not limited to: type 2 membrane receptors such as DC-SIGN, DC-SIGNR, and Langerine; collectins such as pulmonary surfactant proteins (SP-D, SP-Al), mannose binding lectin, and collectin-Kl; and macrophage mannose receptors. In other implementations, the affinity molecule is an antibody.

The affinity particles are anchored to the liposomal surface so their concentration, valency, and distribution can be controlled. This is particularly relevant since pathogen-receptor interactions are often multivalent and the receptor configuration impacts overall avidity. In some implementations, the affinity molecule is attached to an anchor that is incorporated into the lipid bilayer, so the embedded functional groups remain in close proximity but are free to rotate and rearrange. Lipid anchors are favored because the molar ratio of derivatized lipids incorporated can be controlled. Lectins are incorporated by solubalizing a surfactant with pre-formed liposome suspensions, through direct addition of fatty acids to lysine residues, or by modification with hydrophobic anchor lipids such as Nglutaryl-phosphotidylethanolamine (NGPE).

FIG. 8 illustrates an overview of the process of making and using a capture particle. The affinity molecules of FIG. 8A are embedded in the liposome of FIG. 8B to produce a affinity coated liposome as illustrated in FIG. 8C. Next, the capture particle is combined with a blood or other fluid containing undesirable particles. The undesirable particles then bind to the capture particles. FIG. 8E illustrates, bound undesirable particles can then be removed from the fluid by acoustically moving the capture particles whereas unbound undesirable particle are not removed from the fluid.

Figure 9:
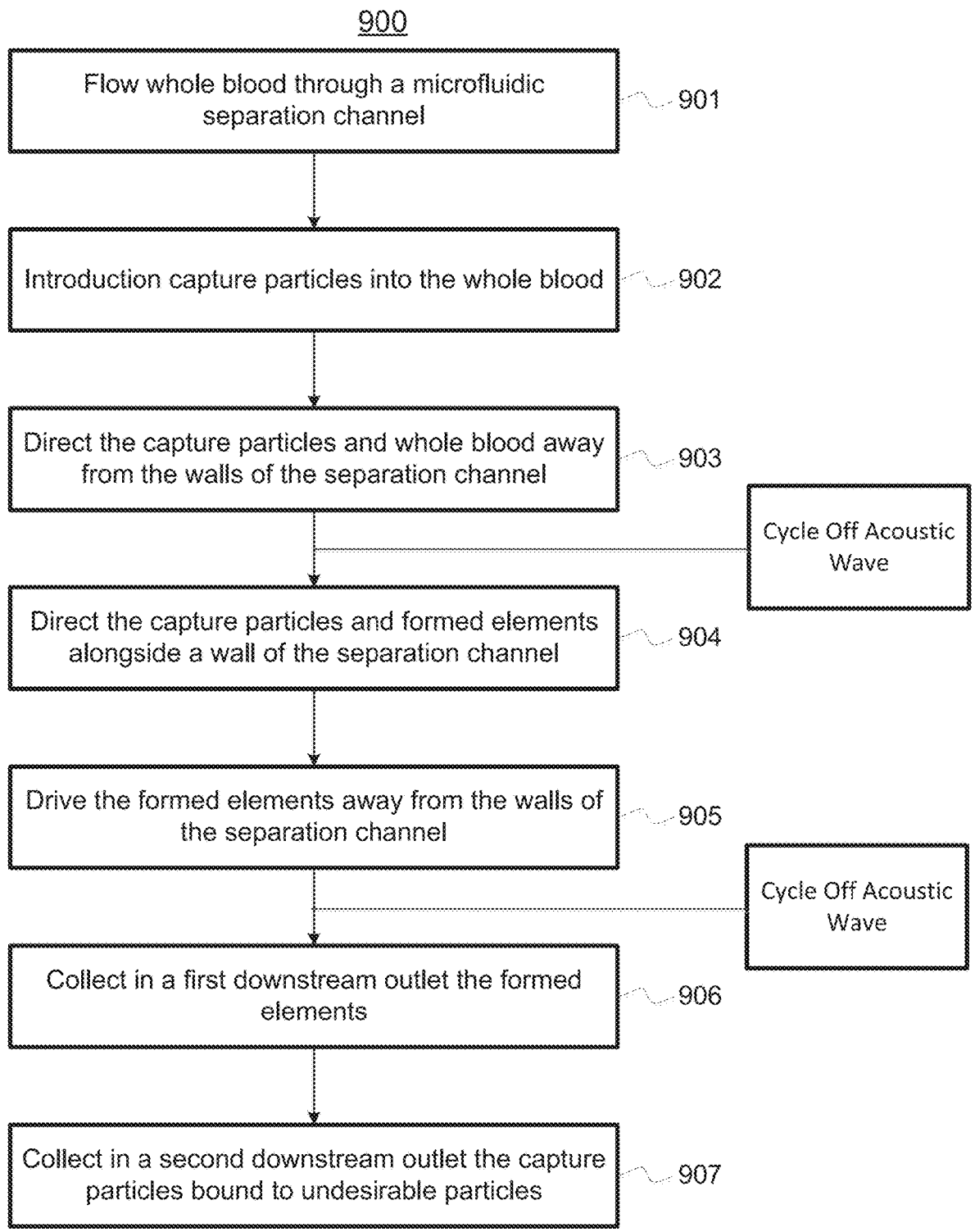
FIG. 9 is a flow chart of a method for cleansing blood with a two-stage separation channel, as depicted in FIG. 3, according to one illustrative embodiment.

FIG. 9 is a flow chart of a method 900 to cleanse blood from undesirable particles in a blood cleaning separation channel similar to the two-stage device described in FIG. 3. First whole blood is flowed through a microfluidic separation channel (step 901). Capture particles are introduced into the whole blood (step 902). Then, formed elements of the blood and the capture particles are directed away from the walls of the separation channel (step 903). Next, the capture particles and formed elements are directed alongside a wall of the separation channel (step 904). Then, formed elements are driven away from the walls of the separation channel (step 905). Finally, the formed elements are collected in a first downstream outlet and the capture particles are collected in a second downstream outlet (steps 906 and 907, respectively).

Referring to FIGS. 3 and 9, the method of cleansing blood includes flowing whole blood through a microfluidic separation channel (step 901). The whole blood contains plasma; a plurality of formed elements such as red blood cells, white blood cells, and platelets; and undesirable particles. In some implementations, the whole blood is flowed through a plurality of microfluidic separation channels, such as the network of channels 300, connected to one another by a manifold system, while in other implementations a single separation channel is used. In some implementations, the whole blood is extracted from a patient. In other implementations the whole blood is collected from a patient or donor and stored prior to cleansing.

Capture particles are introduced into the whole blood (step 902). In some implementations, the capture particles are introduced into the whole blood at the first inlet 301 of the separation channel depicted in FIG. 3. In other implementations, the capture particles are introduced into the device's manifold system or in a mixing chamber upstream from the manifold. After introduction into the whole blood, the capture particles begin to bind to the undesirable particles in the whole blood. For example, a capture particle configured to remove a specific bacteria from the whole blood will selectively bind to the bacteria.

Next, the method 900 continues with the capture particles and the formed elements of the whole blood, which are, originally, substantially-evenly dispersed throughout the whole blood, being directed away from the walls of the separation channel (step 903) and aggregated into alignment at about the center of the separation channel. In some implementations, such as the implementation in the network 300 as described above, this is done with a first bulk transducer 302 imparting a standing acoustic wave across the channel transverse to the direction of flow within the channel in an upstream portion 308, resulting in a pressure node at about the center of the separation channel. In such implementations the contrast factor of the capture particles has the same sign as that of the formed elements, thus the formed elements and capture particles move in tandem towards the pressure node. This initial aggregation of particles along a common axis enables later separation of the capture particles from the formed elements of blood due based on their differential acoustophoretic mobilities.

As discussed above in reference to network 300, after an initial aggregation (step 903), the method 900 continues with the capture particles and formed elements of blood being directed alongside a downstream wall of the separation channel (step 904). In some implementations, such as that of network 300, this is accomplished by a shift in the separation channel such that the downstream portion of the separation channel is significantly aligned with the middle of the upstream portion of the separation channel.

As depicted in FIG. 3 above, in the downstream portion 309, the method 900 continues with the formed elements being driven way from the walls of the separation channel (step 905). As mentioned above, in some implementations, the contrast factor of the formed elements and the capture particles have the same sign but are of different magnitudes. Thus, the formed elements will migrate away from the wall at a faster rate than the capture particles and undesirable particles. In other implementations, the capture particles are designed to have a contrast factor magnitude larger than the formed elements of blood, thus the capture particles move away from the wall at a faster rate than the formed elements.

In some implementations, the standing waves applied to the upstream portion 308 and/or to the downstream portion 309 are periodically halted for a limited amount of time. Doing so allows capture particles or formed elements that may have become trapped against a sidewall of the separation channel 300 to be released, thereby preventing clogging or congestion in the channel. For example, for devices utilizing an excitation frequency of about 1.0 MHz, the standing waves may be halted about once every second for about one tenth of second. In other implementations, the standing waves may be halted more or less frequently with shorter or longer durations depending, for example, on the length and width of the channel and the flow rate of fluid through the channel. In general, the standing wave has a duty cycle of between about 75% and about 98%.

The method 900 concludes when the formed elements are collected in a first downstream outlet (step 906) and the capture particles being collected in a second downstream outlet (step 907). As described above in relation to network 300, the second downstream outlet 306 is configured to collect fluid containing capture particles substantially devoid of formed elements. In some implementations, this is achieved by configuring the width of the second downstream outlet 306 to be slightly less than d(f, x), the distance the formed elements travel in response to the standing acoustic wave given a flow rate off and a distance x from the point of application of the standing acoustic wave. Thus the formed elements, having been driven d(f, x) away from the of the separating channel will be collected in the first downstream outlet 307.

Figure 10:
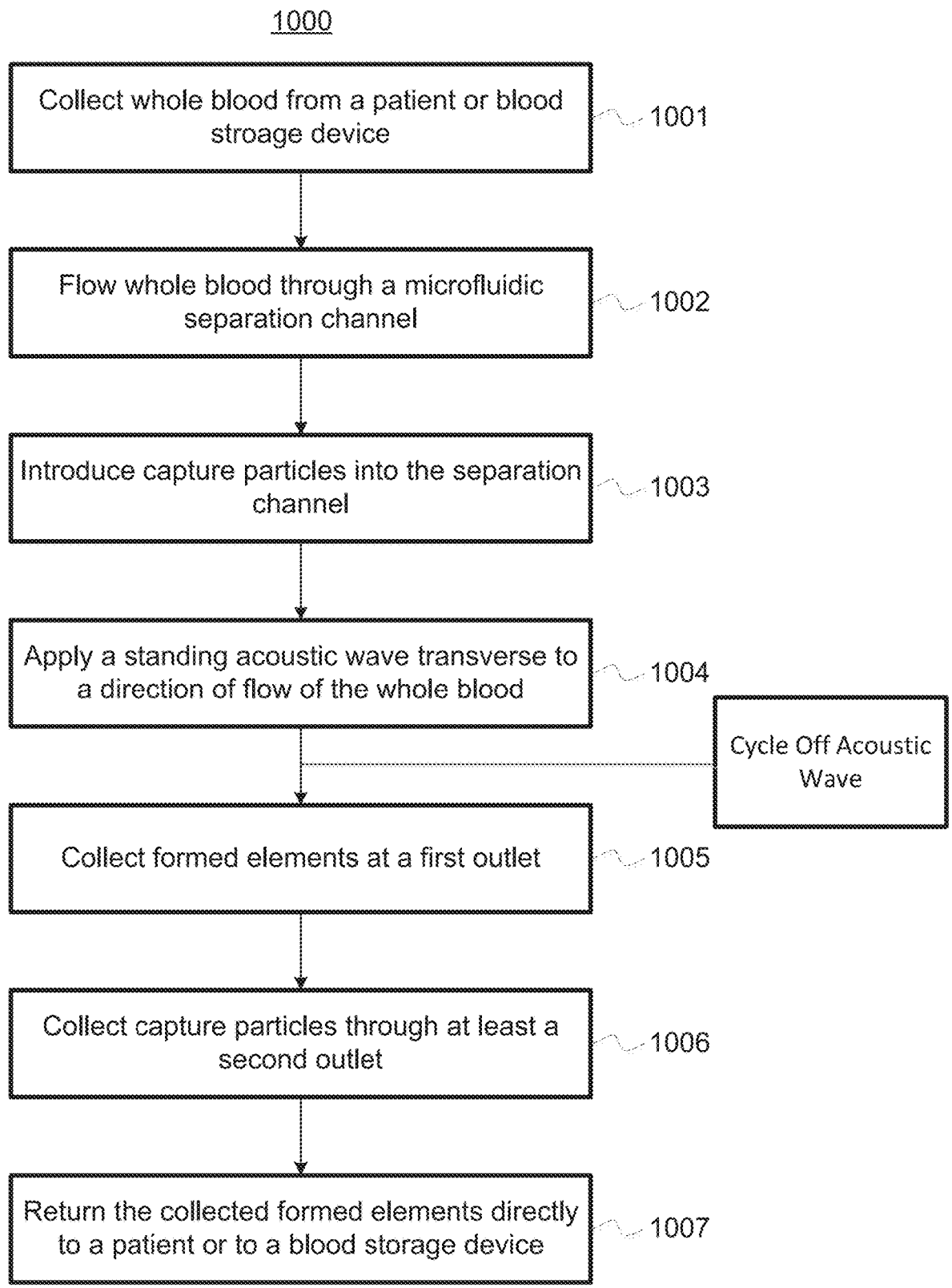
FIG. 10 is a flow chart of a method for cleansing blood with a single-stage separation channel, as depicted in FIG. 2, according to one illustrative embodiment.

FIG. 10 is a flow chart of a method for cleansing blood with a single-stage microfluidic separation channel (1000). First, whole blood is collected (step 1001). Then whole blood is flowed into an inlet of a single-stage microfluidic separation channel, as depicted in FIG. 2 (step 1002). Next, a plurality of capture particles is introduced into the whole blood (step 1003). Then a standing acoustic wave is applied to the separation channel (step 1004). The formed elements are then collected in a first outlet (step 1005). Next, the capture particles are collected in a second outlet (step 1006). Finally, the cleansed blood is returned to a storage container or returned directly to the patient (step 1007).

Referring to FIGS. 1, 2 and 10, the method 1000 of cleansing blood with a single-stage microfluidic separation channel 200 begins by collecting whole blood. In some implementations, the whole blood is collected from a patient 101, and then directly introduced into the blood cleansing system 100. In other implementations, the whole blood is collected from a patient 101 and then stored for later cleansing.

Next, the method 1000 of cleansing blood with a single-stage microfluidic separation channel 200 continues by flowing whole blood into the inlet of a microfluidic separation channel (step 1002). The whole blood contains a plurality of formed elements, plasma, and a plurality of undesirable particles. In some implementations, the undesirable particles can be toxins, bacteria, and/or viruses. In some implementations, a single microfluidic separation channel is used, while in others a plurality of single-stage separation channels is used in conjunction to accommodate greater blood flow throughput.

The method 1000 continues with the introduction of a plurality of capture particles into the whole blood (step 1003). In some implementations, the constituent components of capture particles are injected into a separation channel with a micronozzle and spontaneously form capture particles as injected into the separation channel. In other implementations, the capture particles are prefabricated and then introduced into the whole blood. In some implementations, the capture particles are introduced into the whole blood after the whole blood enters the separation channel through the first inlet 202. In yet other implementations, the capture particles are introduced into the whole blood before the blood enters through the first inlet 202 of the separation channel 200. In some implementations, the capture particles are microbeads and/or lipid based liposomes.

Next, the method 1000 continues with the applying of a standing acoustic wave to the separation channel (step 1004). The standing acoustic wave is applied transverse to a direction of flow of the whole blood through the separation channel 200. In some implementations, the formed elements and capture particles have contrast factors with different signs. Thus, the application of the standing acoustic wave causes the formed elements to aggregate about the central axis of the separation channel and the capture particles to aggregate along at least one wall of the separation channel, as depicted in FIG. 2. In other implementations the standing acoustic wave causes the formed elements to aggregate along at least one wall of the separation channel and the capture particles to aggregate about the central axis of the separation channel.

In some implementations, the standing wave is periodically halted for a limited amount of time. Doing so allows capture particles or formed elements that may have become trapped against a sidewall of the separation channel 200 to be released, thereby preventing clogging or congestion in the channel. For example, for devices utilizing an excitation frequency of about 1.0 MHz, the standing wave may be halted about once every second for about one tenth of second. In other implementations, the standing wave may be halted more or less frequently or for shorter or longer durations depending, for example, on the length and width of the channel and the flow rate of fluid through the channel. In general, the standing wave has a duty cycle of between about 75% and about 98%.

Then, the method 1000 continues with the collecting of the formed elements of the whole blood in a first outlet (step 1005). In some implementations, as depicted in FIG. 2, a first outlet 204 is aligned with the central axis of the separation channel allowing the outlet to collect the formed elements as they aggregate and flow down the central axis of the separation channel. Similarly, the method continues with the collecting of the capture particles in a second outlet (step 1006). In some implementations, the end of the separation channel has at least a second outlet channel 206 and 207 aligned with at least one wall of the separation channel. As the capture particles are driven towards the antipressure notes along the walls of the separation channel, they are collected by the outlets channels 206 and 207 aligned with the walls of the separation channels. In some implementations, the standing acoustic wave is adjusted such that the formed particle align along the walls of the separation channel and the capture particles align with the central axis of the separation channel. In such an implementation, the formed elements are funneled into outlets along the wall of the separation channel and the capture particles are funneled into an outlet aligned with the central axis of the separation channel. In some implementations, the outlet channels 206 and 207 terminate in individual outlets or merge to terminate into a single outlet 205.

The method 1000 concludes with the reintroduction of the cleansed blood into a patient 101 or storage (step 1007). In some implementations, such as system 100, the whole blood is collected directly from a patient and then reintroduced to the patient 101. In some implementations, the cleansed blood is reheated to body temperature before being reintroduced into the patient 101. In other implementations, the cleansed blood is collected in a storage container for later reintroduction into a patient 101.

What is claimed is:

1. A blood cleansing device comprising:
   a microfluidic separation channel defined in a thermoplastic and having an upstream end and downstream end, the microfluidic separation channel comprising:
   a first inlet configured to introduce flowing whole blood into a proximal end of the microfluidic separation channel, the whole blood including plasma, a plurality of formed elements and a plurality of undesirable particles;
   a first outlet at the downstream end of the microfluidic separation channel positioned substantially along a longitudinal axis of the microfluidic separation channel;
   a second outlet at the downstream end positioned adjacent a first wall of the microfluidic separation channel; and
   an acoustic transducer positioned adjacent to the microfluidic separation channel and configured to operate at a predetermined frequency to generate a standing acoustic wave across a particle migration region of the microfluidic separation channel, wherein a width of the microfluidic separation channel is between about 25% and 35% of an acoustic wavelength in the whole blood at the predetermined frequency.

2. The blood cleansing device of claim 1, wherein the width of the microfluidic separation channel is between about 30% and about 35% of the acoustic wavelength in the whole blood at the predetermined frequency.

3. The blood cleansing device of claim 1, wherein a thickness of a wall material of the microfluidic separation channel is between about 35% and about 45% of the acoustic wavelength in the wall material at the predetermined frequency.

4. The blood cleansing device of claim 1, wherein the standing acoustic wave is generated in a direction substantially transverse to the longitudinal axis of the microfluidic separation channel.

5. The blood cleansing device of claim 1, further comprising a capture particle injector configured to introduce a plurality of lipid-based capture particles into the whole blood before the whole blood reaches the particle migration region of the microfluidic separation channel.

6. The blood cleansing device of claim 5, comprising a reservoir in fluidic communication with the capture particle injector.

7. The blood cleansing device of claim 6, wherein the reservoir contains the plurality of lipid-based capture particles.

8. The blood cleansing device of claim 6, wherein the reservoir contains a mixture of materials, which when directed by the capture particle injector into the whole blood, form the plurality of lipid-based capture particles.

9. The blood cleansing device of claim 8, wherein the mixture of materials comprises an affinity molecule, a lipid, and a fluid with a density less than about 1 g/cm3.

10. The blood cleansing device of claim 5, wherein the plurality of lipid-based capture particles have significantly different acoustophoretic mobility than that of formed elements of blood.

11. The blood cleansing device of claim 5, wherein the capture particle injector comprises a microfluidic nozzle.

12. The blood cleansing device of claim 5, wherein the capture particle injector comprises a porous membrane.

13. The blood cleansing device of claim 1, wherein the second and third outlets merge at a fourth outlet.

* * * * *